(12) United States Patent
Farina et al.

(10) Patent No.: US 6,645,737 B2
(45) Date of Patent: Nov. 11, 2003

(54) METHOD FOR MAINTAINING TEST ACCURACY WITHIN A MICROBIOLOGICAL TEST ARRAY

(75) Inventors: Edward Francis Farina, Oxford, PA (US); Edward Stephen Kaminski, Elkton, MD (US); John Charles Mazza, Newark, DE (US); Bruce McLean Gemmell, Wilmington, DE (US); William David Dunfee, New Castle, DE (US)

(73) Assignee: Dade Microscan Inc., West Sacramento, CA (US)

( * ) Notice: Subject to any disclaimer, the term of this patent is extended or adjusted under 35 U.S.C. 154(b) by 84 days.

(21) Appl. No.: 09/841,029

(22) Filed: Apr. 24, 2001

(65) Prior Publication Data

US 2002/0155515 A1 Oct. 24, 2002

(51) Int. Cl.$^7$ .................................................. C12Q 1/18
(52) U.S. Cl. ...................................... 435/32; 435/288.5
(58) Field of Search .............................. 435/32, 29, 30, 435/288.4, 288.5, 305.3; 422/58, 63

(56) References Cited

U.S. PATENT DOCUMENTS

| | | | | |
|---|---|---|---|---|
| 4,704,255 A | | 11/1987 | Jolley ........................ 422/101 |
| 4,908,112 A | * | 3/1990 | Pace ....................... 204/299 R |
| 5,609,828 A | | 3/1997 | O'Bear et al. .............. 422/102 |
| 5,679,310 A | | 10/1997 | Manns ........................ 422/102 |
| 5,746,980 A | | 5/1998 | O'Bear et al. .............. 422/102 |
| 5,766,553 A | | 6/1998 | Staples et al. .............. 422/102 |
| 5,922,593 A | | 7/1999 | Livingston ............... 435/288.5 |
| 5,932,177 A | | 8/1999 | O'Bear et al. .............. 422/102 |
| 6,096,562 A | * | 8/2000 | Bunn et al. ................. 436/518 |
| 6,251,662 B1 | * | 6/2001 | Day ........................ 435/288.3 |
| 6,326,211 B1 | * | 12/2001 | Anderson et al. ........... 436/177 |

FOREIGN PATENT DOCUMENTS

| | | | |
|---|---|---|---|
| WO | WO 99/44742 | * | 9/1999 |
| WO | WO 01/92461 A1 | * | 12/2001 |

* cited by examiner

*Primary Examiner*—Ralph Gitomer
(74) *Attorney, Agent, or Firm*—Leland K. Jordan

(57) ABSTRACT

A microbiological test array with a plurality of microwells connected by a microchannel to a solution reservoir. Subsequent to filling the microwells, the microchannels are sealed to protect the integrity of the solution in the test microwells.

11 Claims, 13 Drawing Sheets

METHOD FOR MAINTAINING TEST ACCURACY WITHIN A MICROBIOLOGICAL TEST ARRAY

FIELD OF THE INVENTION

The present invention relates to methods using microbiological test arrays having a number of microwells in automated analyzers. More particularly, the present invention provides a method for maintaining the integrity of a of liquid test solution within the individual microwells.

BACKGROUND OF THE INVENTION

Various types of tests related to patient diagnosis and therapy can be performed by analysis of a biological sample. Biological samples containing the patient's microorganisms are taken from a patient's infections, bodily fluids or abscesses and are typically placed in test panels or arrays, combined with various reagents, incubated, and analyzed to aid in treatment of the patient. Automated biochemical analyzers have been developed to meet the needs of health care facilities and other institutions to facilitate analysis of patient samples and to improve the accuracy and reliability of assay results when compared to analysis using manual operations. However, with ever changing bacterial genera and newly discovered antibiotics, the demand for biochemical testing has increased in both complexity and in volume. Because of these greater demands in conjunction with the expense and scarcity of floor space within health care institutions and the pressure to provide clinical results at lower costs, it has become important to simultaneously perform various types of biochemical tests within a highly automated and compact analyzer that operates with minimal clinician attention using cost-effective techniques.

An important family of automated microbiological analyzers function as a diagnostic tool for determining an antibiotic effective in controlling growth of the microorganism. In performing these test, in vitro antimicrobic susceptibility patterns of microorganisms isolated from biological samples are ascertained. Such analyzers have historically placed selected biochemicals into a plurality of small sample test wells in panels or arrays that contain different antimicrobics against known microorganisms in serial dilutions. Minimum Inhibitory Concentrations (MIC) of antibiotics effective against the microorganism are determined by color changes, fluorescence changes, or the degree of cloudiness (turbidity) in the sample test wells created in the arrays. By examining the signal patterns generated, MIC analyses are performed by computer controlled microbiological analyzers to provide advantages in reproducibility, reduction in processing time, avoidance of transcription errors and standardization for all tests run in the laboratory.

The use of microbiological test trays and the techniques employed in MIC tests, also known as antibiotic susceptibility testing, AST, of microorganisms are also well known. AST tests are essentially broth dilution susceptibility tests using wells filled with inoculum and a growth broth, called herein a inoculum-broth solution, and increasing concentrations of a number of different antibiotics, or antimicrobial agents. The different antimicrobial agents are typically diluted in Mueller-Hinton broth with calcium and magnesium in chromogenic panels or diluted in autoclaved water with a fluorogenic compound in fluorogenic panels. The antimicrobials are diluted to concentrations that include those of clinical interest. After incubation, the turbidity or fluorescence will be less or non-existent in wells where growth has been inhibited by the antimicrobics in those wells. The analyzer compares each test well reading with a threshold value. The threshold value is a fixed number corresponding to a certain percentage of relative absorbency or fluorescence which corresponds to clinically significant growth. The MIC of each antimicrobial agent is measured either directly as visible growth, or indirectly as an increase in fluorescence.

Important challenges that must be taken into consideration when designing cost-effective, automated biochemical analyzers include the volume of reagents required per test and the cost of the disposable test panel, array or, in certain designs, a centrifugal test rotor. Because they are small and may be produced using mass-production, plastic injection molding techniques, it is advantageous to use very small sized test arrays having a number of microwells for performing AST tests in order to facilitate automatic handling and minimize the expense of a disposable test array. AST test arrays typically consist of a plurality of adjacent microwells aligned in some sort of an array that function as reaction vessels for the above mentioned biochemical reactions involving a solid phase media and a liquid phase containing a sample to be tested. An aliquot of the sample is placed in each microwell along with appropriate antibiotic reagents. AST testing usually requires that the test trays be incubated at a controlled temperature for a period of time so that an observable reaction between the sample and reagent occurs; at predetermined time intervals, each microwell of the test tray is examined for an indication of changes in color change, turbidity, or size.

Filling the number of microwells with the required inoculum and/or reagents presents several technical challenges that are made increasingly difficult as the size of the microwells is reduced. These challenges include providing a uniformity of fill, maintaining an absence of air bubbles that impede test observations, controlling adverse evaporation effects, maintaining the integrity of test observations, etc. Efforts have been made to address these challenges along with other problems and these generally employ a vacuum technique in filling microwells within a test array via an interconnected number of micro-sized channels connected between the microwells and an inoculum reservoir.

U.S. Pat. No. 5,932,177 provides a test sample card as typically used in biochemical analysis, having a number of same-sized rectangular shaped sample wells and fluid flow by means of a plurality of through-channels which route the fluid flow of samples along both the front and back surfaces of the card. Elevated bubble traps are provided, as are integral interrupt slots for sensing card position and alignment.

U.S. Pat. No. 5,922,593 discloses a microbiological test panel having a plurality of translucent cups extending from a first side of a planar surface, and a chassis having a plurality of open-ended tubes formed in the chassis. The chassis includes a plurality of raised passage walls on a second side of the planar surface that form passageways over the openings at the bottom ends of the tubes. One end of the passageway has an opening to allow an inoculum to flow through the passageway. The chassis further comprises an air communication port formed as an open-ended tube extending from the second side of the planar surface.

U.S. Pat. No. 5,766,553 discloses a molded test sample card comprising a fluid entrance port and first and second end regions and first and second side regions. A plurality of growth or reaction wells are located in the card body between the first and second end regions and the first and second side regions. A fluid channel network connects the fluid entrance port to said growth wells. To improve the flow of the material during the molding process, cored regions are disposed in at least one of the first and second end regions or the first and second side regions.

U.S. Pat. No. 5,746,980 discloses a test sample card with a fluid intake port and sample wells disposed between its opposite surfaces. A fluid channel network connects the fluid intake port to the sample wells and a bubble trap is connected to at least one of the sample wells by a conduit with formed in said first surface of the card. The bubble trap is formed as a depression extending part way through the card body and is covered by sealant tape.

U.S. Pat. No. 5,679,310 discloses a microtiter plate formed of a substantially rigid, polymeric plate having a substantially flat upper surface and a array of cylindrical or frusto-conical wells. The well bottom is either fluid impervious or pervious. In embodiments with fluid pervious well bottoms, a vacuum plenum is provided below the wells for drawing fluid from the wells through the pervious material.

U.S. Pat. No. 5,609,828 discloses a sample card with an intake port and a first fluid flow distribution channel connected to the intake port to distribute a fluid sample from the intake port to a first group of sample wells and a second fluid flow distribution channel to distribute a fluid sample from the intake port to a second group of wells.

U.S. Pat. No. 4,704,255 discloses an assay cartridge which has a substantially rectangular base plate, a substantially rectangular top plate, and four sidewalls. The top plate has a plurality of reaction wells on its top side. A port through the base plate allows reducing the pressure in the waste reservoir relative to the pressure over the wells to draw the liquid phase of a reaction from the well through the filter and into the waste reservoir.

From this discussion, it may be seen that there remains a need for a test tray that simply and inexpensively solves the above described technical challenges. In particular, there is a need for a simple and inexpensive microbiological test array in which all the test wells contained therein may be quickly filled with a microbiological sample for AST testing in a manner that maintains the integrity of an original test sample in a filled microwell without additional test sample entering therein.

SUMMARY OF THE INVENTION

The present invention meets the foregoing needs by providing a microbiological test array having a plurality of microwells prefilled with known amounts of different antibiotics that can be easily and securely filled with sample and used for AST testing. One particular embodiment of the present invention is directed at a microbiological test array with a generally flat lower surface having a plurality of upwardly projecting microwells, the microwells being connected by a number of microchannels to an open reservoir formed in a upper surface of the test array. The end of the reservoir nearest the microwells has an opening to permit a liquid inoculum-broth solution to flow from the reservoir to each of the microwells. Solution is moved during filling from the reservoir through a reservoir microchannel having an air vent port adapted to control a vacuum filling process, first into a sacrificial evaporation well and therefrom into a conduit microchannel connected to a number of feeding microchannels, each single one being connected to each single one of the plurality of microwells. Subsequent to the vacuum filling process, each one of the number of feeder microchannels is sealed from the conduit microchannel, thereby protecting the integrity of the inoculum-broth solution in the test microwells. Alternately, the feeding microchannels may be filled with an inert sealing material like silicone or gas to prevent the flow of unwanted inoculum-broth solution into the microwells.

BRIEF DESCRIPTION OF THE DRAWINGS

These and other features and advantages of the present invention can best be understood by reference to the detailed description of the preferred embodiments set forth below taken with the drawings in which.

DETAILED DESCRIPTION OF THE PREFERRED EMBODIMENTS

Figure 1:
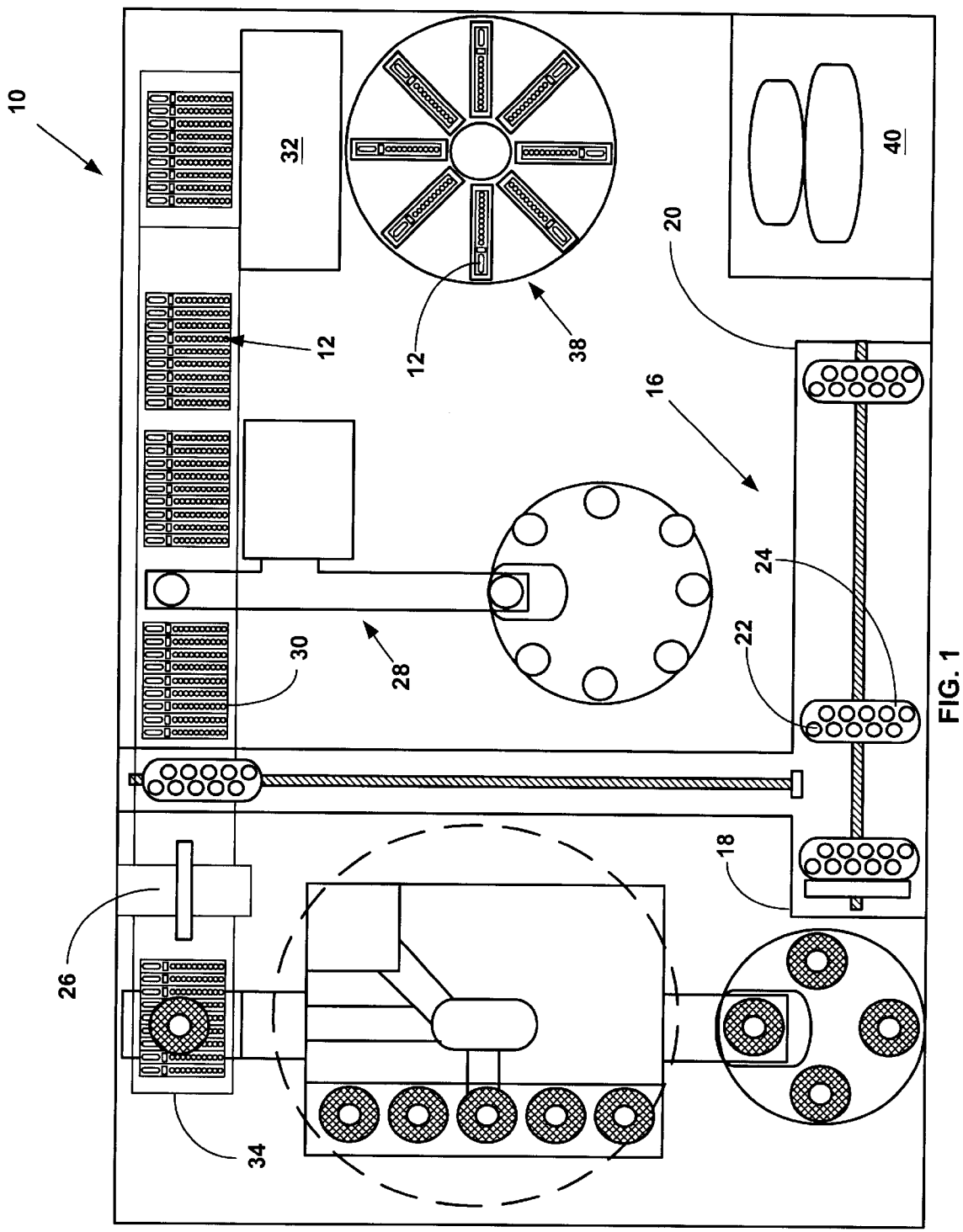
FIG. 1 is a simplified schematic plan view of an automated microbiological analyzer in which the test array of the present invention may be used.

FIG. 1 schematically illustrates a multifunctional automated microbiological analyzer 10 wherein the microwell test array 12 of the present invention may be used for receiving and storing reagents and for supporting biochemical reactions using test samples to be tested and analyzed. Antimicrobial Minimum Inhibitory Concentrations (MIC), also identified herein as Antibiotic Susceptibility Testing (AST), are determined by measuring color, fluorescence, or the degree of turbidity of a biochemical reaction between test samples and various antimicrobials which have been diluted to concentrations that include those of clinical interest and supplied to the different microwells within AST test array 12 during manufacture. An AST incubation and optical measuring station 14 may be adapted to conduct conventional AST tests using methods known in the art.

An AST microwell test array 12 may be transported throughout analyzer 10 using an automated transport system 16 having an input portion 18 and an output portion 20 located at the front of analyzer 10 in FIG. 1 for the various purposes described herein. Transport system 16 comprises three separate segments adapted to transport test tubes 22 supported in a tube rack 24 and containing an inoculum of microorganisms isolated from biological specimens and having a bacteria concentration within a predetermined operable range. Transport system 16 moves each rack 24 to the rearmost portion of analyzer 10 where a translatable pipetting system 26 aspirates inoculum and dispenses a predetermined quantity of inoculum into a broth cup having a known solution of, for example, Mueller-Hinton broth. This inoculum-broth solution is mixed, aspirated and dispensed into a reservoir described hereinafter contained within an AST array 12 at an inoculum-broth dispensing station 28.

A number of AST arrays 12 may be carried using an AST array carrier 30 that is also transported by transport system 16 along the rearmost portion of analyzer 10 seen in FIG. 1 between the inoculum-broth dispensing station 28, an array carrier loading station 32, an AST array filling station 34, an AST array loading station 36 and an AST array disposal station (not shown). When an array carrier 30 is to be loaded at the array carrier loading station 32 with untested AST arrays 12, arrays 12 are moved to the carrier 30 by a feeding mechanism (not shown) from an AST array storage carousel 38 which contains a number of unfilled AST arrays 12. After a carrier 30 is fully loaded with unfilled AST arrays 12, the array carriers 30 are transported to the inoculum-broth dispensing station 28 where an amount of inoculum-broth solution is dispensed into an inoculum-broth solution receiving reservoir described hereinafter within each individual AST array 12; the arrays 12 are subsequently transported to the array filling station 34 where the inoculum-broth solution is dispersed uniformly to all test microwells in the individual arrays 12 using vacuum means described hereinafter.

Broth is supplied to the analyzer 10 in an appropriate container so that when an AST array 12 is to be filled with inoculum-broth solution, a known amount of inoculum is pipetted using translatable pipetting system 26 from a sample test tubes 22 into a broth container, mixed, and then aspirated from the broth container into the aforementioned inoculum-broth solution receiving reservoir 50 of individual test arrays 12.

After a number of individual AST microwells 44, described hereinafter in conjunction with FIG. 2 and formed within AST test arrays 28 seen in FIG. 1, are loaded with inoculum-broth solution, each of the individual AST microwells 44 is sealed to prevent additional flow of inoculum-broth solution thereinto; AST arrays 12 are then incubated at elevated temperatures for different lengths of time, depending upon test conditions, during which a number of test readings are conducted. Test readings may be obtained using any number of known means, including using optical methods in which light that has been passed through an interference filter is guided through the top of the AST microwells 44 of the array 12 using lens or optical fiber channels. Light-sensitive photodiodes or the like detect the amount of light passing through each microwell and generate a electronic signal corresponding to the degree of turbidity within each. Antimicrobics are present in specified different concentrations in different microwells 44 of AST test arrays 12. The turbidity will be less or non-existent in wells where growth has been inhibited by the antimicrobic. Thus, the intensity of light generated by a light source and captured by a detector after transmission through each microwell 44 is inversely proportional to the concentration of bacteria in that well. Alternately, using a fluorometer system, the intensity of the fluoresence in each microwell 44 is proportional to the concentration of bacteria in that well. In addition, selected microwells 44 may contain biochemical substrates which exhibit a color change or fluoresence in the presence of certain bacteria. A colorimetric or fluorometric measurement, yields information about the solution in the well. The optical information generates a corresponding electrical signal which is then converted to computer-compatible digital form and stored in computer memory. The digital information is used by a Central Processing Unit (CPU) 40 having commands and control circuitry which are programmed to control all aspects of devices within analyzer 10. After a test array 12 has been optically analyzed and the values stored, each microwell 44 test reading is compared with a threshold value corresponding to a certain percentage of relative absorbency or fluorescence which is found to correspond to clinically significant growth. These signals are then processed by the CPU 40 by comparing them to stored control values, thereby calculating the AST pattern. In this way, the MIC of each antimicrobic is determined.

Figure 2:
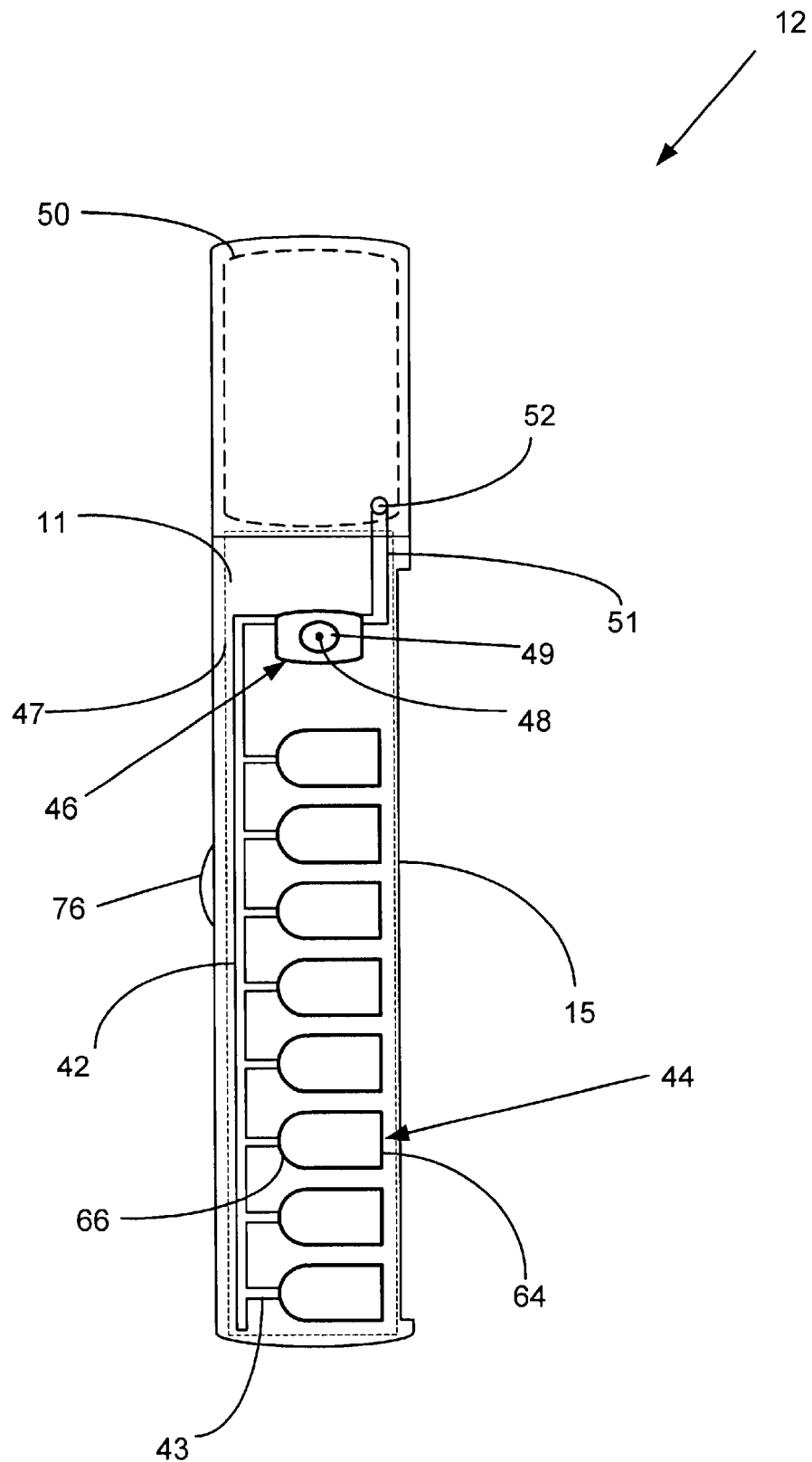
FIG. 2 is a bottom plan view of a test array useful in the microbiological analyzer of FIG. 1.
Figure 3:
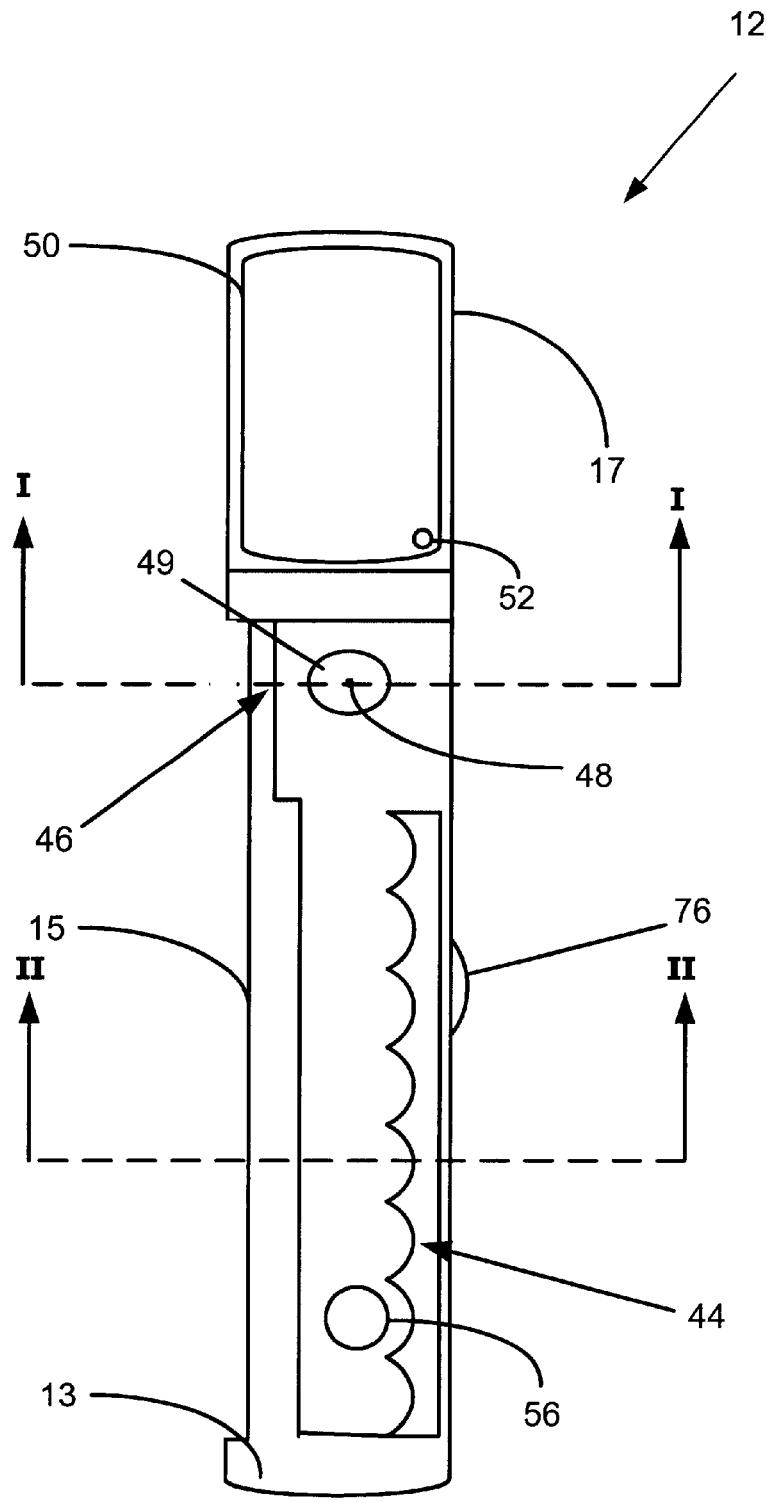
FIG. 3 is a top plan view of the test array of FIG. 2.
Figure 4:
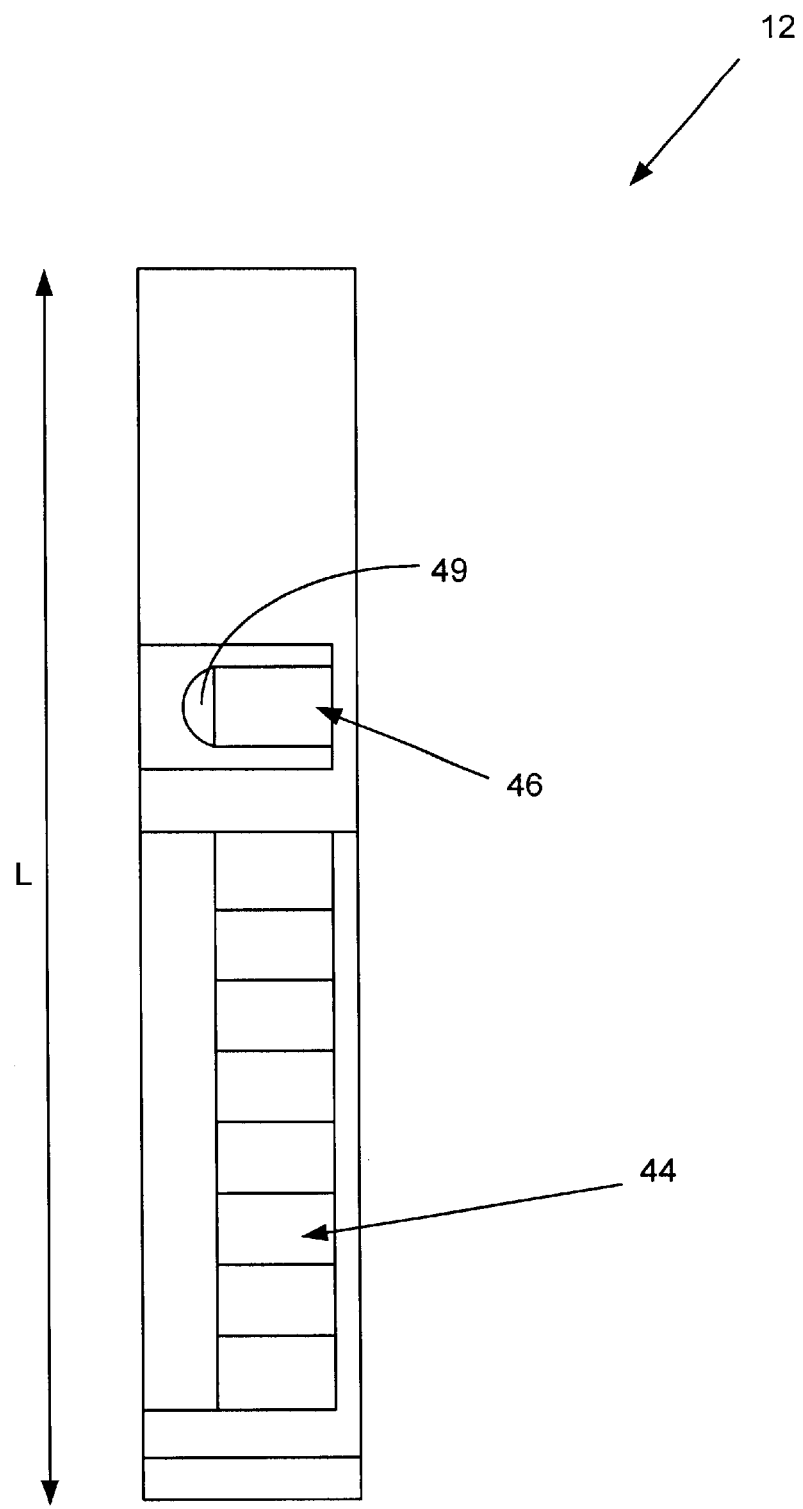
FIG. 4 is an elevational side view of the test array of FIG. 2.

As seen in the embodiment of the present invention illustrated in FIG. 2 showing the lower bottom surface 11 of an AST array 12 as being relatively flat, and in FIG. 3 showing the upper top surface 13 of the AST array 12 as containing relatively structured features described hereinafter. Each AST array 12 has an elongate length L and a plurality of upwardly projecting microwells 44 formed in the bottom surface 11 as a linear row of single microwells 44 parallel to the length and is therefore of a generally elongate rectangular shape having the bottom surface 11 and top surface 13 on opposing sides, the opposed surfaces being separated by an indented sidewall 15 and an opposed second sidewall 17. Array 12 includes a plurality of upwardly projecting AST microwells 44 disposed in the bottom surface 11 along the elongate length L (FIG. 4) of the array 12 to form a single linear row of individual microwells 44. The individual microwells 44 are connected by a number of short filling microchannels 43 to a single conduit microchannel 42 to a sacrificial evaporation well 46 formed in the bottom surface 11 of the test array upwardly projecting from an open portion of the bottom surface 11 and disposed between the row of microwells 44 and a reservoir 50 described hereinafter. The evaporation well 46 is also seen in FIG. 4 as having a closed dome-shaped upper surface 49 proximate the top surface 13 of the test array with a sealable vacuum port 48 formed therein as an opening in a dome-shaped upper surface 49 of the evaporation well 46 (FIG. 3, section A—A). Microwells 44 have the general shape of a closed well projecting upwards from the bottom surface 11 of the array 12 with a depth of about three-fourths the thickness of array 12, and have openings along the bottom surface 11 of array 12.

As seen in FIG. 2, reservoir microchannel 51 is formed as a open groove in the bottom surface 11 of the array 12 and connects the evaporation well 46 to a rectangular shaped inoculum-broth solution receiving reservoir 50 best seen in FIG. 3, the reservoir 50 having an open top and a closed bottom illustrated by dashed lines in FIG. 2. One end of the bottom of the reservoir 50 has a flow opening 52 also illustrated by dashed lines in FIG. 2. to allow an inoculum-broth solution dispensed into the top of reservoir 50 to flow from reservoir 50 through reservoir microchannel 51, firstly to the sacrificial evaporation well 46 and then through a conduit microchannel 42 sequentially to each of the series of microwells 44 through short filling microchannels 43. The open surface portions of microchannels 51, 42 and 43, flow opening 52, sacrificial evaporation well 46, and microwells 44 along the bottom surface of array 12 may be closed by sealing over with a layer of adhesive sealant tape 47, shown in dashed lines, during a manufacturing process in which predetermined amounts of antimicrobial agents of clinical interest are placed in the different microwells 44 but not in the sacrificial evaporation well 46. Optionally, one well may be left empty of antimicrobics so that it may be used as a reference.

In an exemplary embodiment of the present invention as illustrated in FIG. 3 showing the top view of an AST array 12, taken in conjunction with FIG. 2, each AST array 12 comprises a singulated linear row of eight individual microwells 44 connected by the linear microchannel 42 which is formed in the bottom surface 11 of the AST array 12, best seen in FIG. 2. Microchannel 42 is aligned parallel to the row of microwells 44 and is connected to each microwell 44 by short microchannel 43. Microchannel 42 further connects the microwells 44 to the sacrificial evaporation well 46 disposed between one end of the row of microwells 44 and the inoculum-broth solution receiving reservoir 50. Sacrificial evaporation well 46 may be seen in cross-section view A—A of FIG. 3 seen in FIG. 3A and in FIG. 2B (upwards view from bottom) as comprising a pair of mutually opposed parallel endwalls 68 connected by a pair of mutually opposed parallel sidewalls 72. Endwalls 68 are shorter than sidewalls 72 and endwalls 68 and sidewalls 72 are substantially perpendicular to the bottom surface 11 of test array 12. The upper surfaces of endwalls 68 and sidewalls 72 are connected by a cone-shaped upper surface 49 to form a small generally rectangular evaporation chamber 70 enclosed by sacrificial well 46. An important feature of sacrificial well 46 is the sealable vacuum port 48 formed as an opening in the cone-shaped upper surface 49 that enables air to be evacuated from sacrificial well 46 and to be evacuated from microchannels 42 and 43 and be evacuated from microwells 44 during an inoculum-broth filling operation described hereinafter. Evaporation chamber 70 is typically sized to accommodate an amount of inoculum-broth solution in the 0.02 to 0.04 mL range.

Figure 2A:
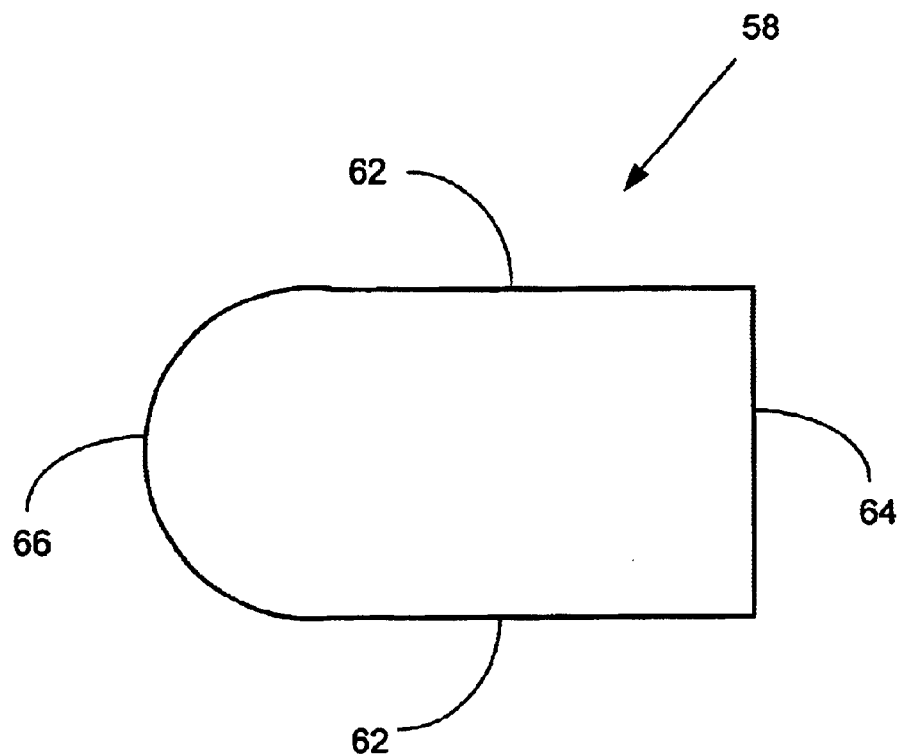
FIG. 2A is an enlarged bottom view of a portion of the test array of FIG. 2.
Figure 3A:
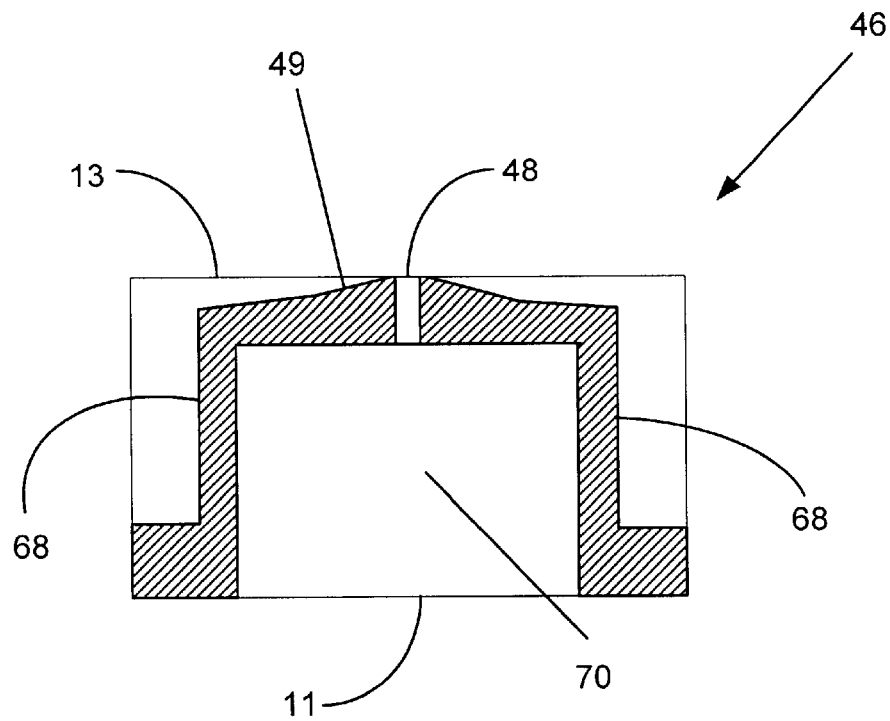
FIGS. 3A and 3B are cross-sectional views of the test array of FIG. 3.
Figure 3B:
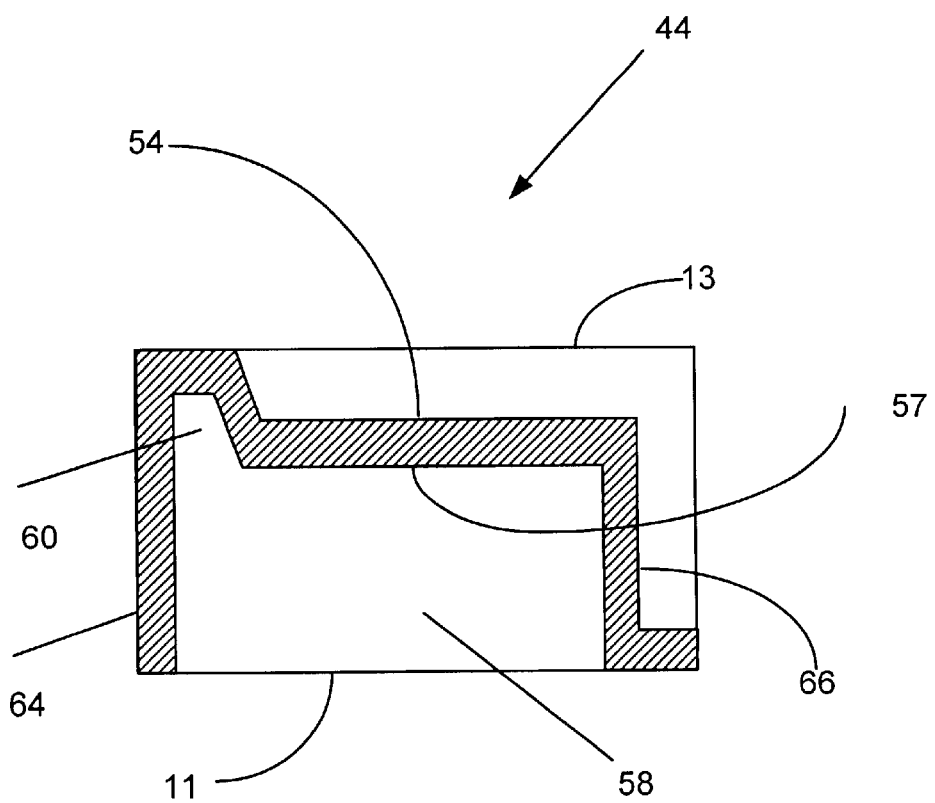
Figure 5:
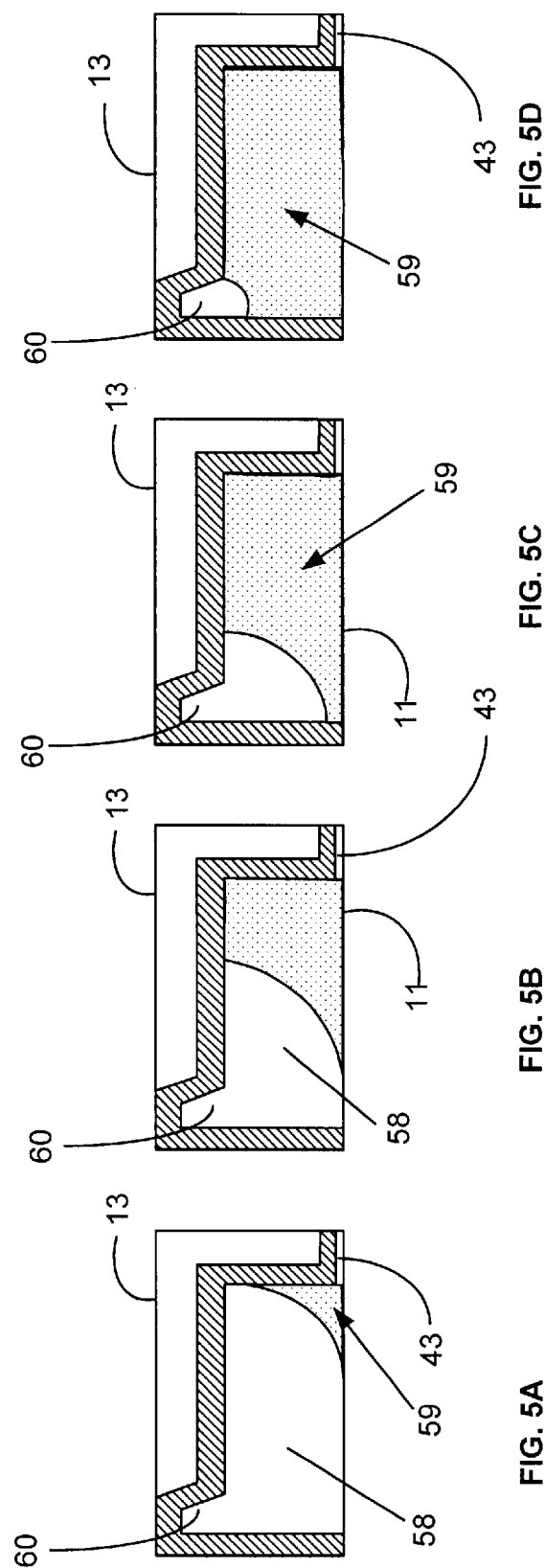
FIGS. 5A–B–C–D are illustrative of a microwell filling process using the test array of FIG. 2.

Cross-section B—B in FIG. 3B illustrates the microwells 44 as having a solid irregular top surface 54 portion of array 12, a rounded endwall portion 66 (also see FIG. 2A) of the sidewall 17, a flat endwall portion 64 (also see FIG. 2A) of the indented sidewall 15 and two parallel sidewalls 62. Both endwalls 66 and 64 are formed substantially perpendicular to the lower bottom surface 11 of array 12 and are separated by the two parallel sidewalls 62. The irregular top surface, the flat endwall portion 64, and the rounded endwall portion 66 cooperate to define a small AST test chamber 58. The irregular top surface 54 is shaped to form a recessed top edge portion of AST test chamber 58 adapted to act as a bubble trap 60 for bubbles that may be generated as a inoculum-broth solution is dispensed through microchannel 42 from reservoir 50 to all test microwells 44 in an array 12. It has been unexpectedly found that when microwell 44 is shaped as described herein, then if the microchannel 43 is positioned on the opposite surface of microwell 44 across from the bubble trap 60, the bubble trap 60 is effective in capturing bubbles when microwell 44 is comprised of a generally hydrophilic material, like styrene. It has been observed that with such an arrangement, as inoculum-broth solution, illustrated as 59 in FIGS. 5A–C–D flows into microwell 44, any air remaining within microwell 44 is urged by the expanding inoculum-broth solution without leaving any entrapped air pockets in the critical upper central area of the test chamber 58. Such a filling is pictorially illustrated in FIGS. 5A–B–C–D. Thus, air is removed away from the central area of the top surface 54 through which a beam of interrogating radiation may pass as described hereinafter without requiring bubble traps separate from the chamber 58 or bubble traps with complex valve features.

Figure 2B:
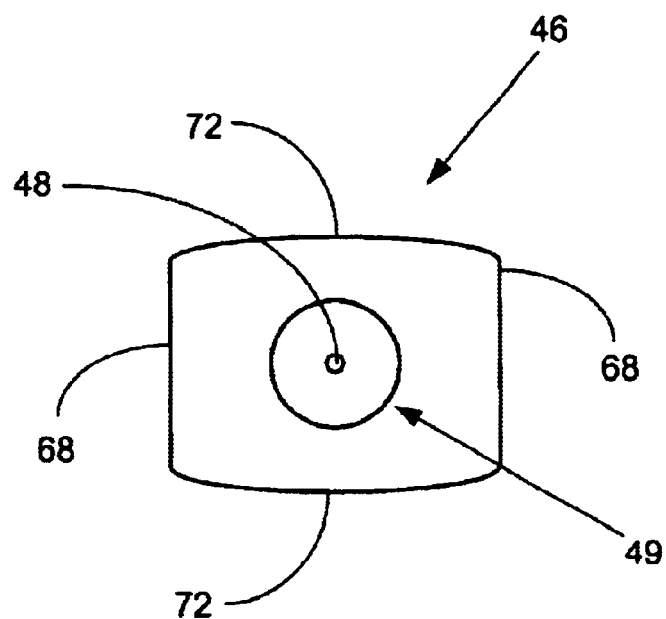
FIG. 2B is an enlarged bottom view of a portion of the test array of FIG. 2.

AST test chamber 58 is typically sized to accommodate an amount of inoculum-broth solution in the 0.03 to 0.04 mL range. As also seen in FIG. 2A, each microwell 44 has a generally elongate shaped lateral cross-section with two parallel sidewalls 62, the generally flat endwall portion 64 perpendicular between the parallel sidewalls 62 and the generally rounded front wall 66 also between the two parallel sidewalls 62. In a preferred embodiment, the upper top surface 13 and lower bottom surface 11 are about 0.3–0.4 inches wide, the indented sidewall 15 is about 0.2–0.25 inches in height and the elongate dimension of the test array 12 is about 2.5–3.0 inches in length. In such an embodiment, the microchannel 42 would be sized with a width and depth of about 0.010 to 0.020 inches.

The sacrificial evaporation well 46 seen in FIG. 3A is designed to accomplish two important purposes: firstly, provision of a evaporation chamber 70 from which sacrificial evaporation of inoculum-broth solutions may take place, thereby inhibiting evaporation of solution from microwells 44. Evaporation from microwells 44 is inhibited because evaporation initially must occur from within reservoir microchannel 51 and then from the sacrificial evaporation chamber 70 before evaporation might occur from microchannels 42 and 43 and microwells 44. Evaporation chamber 70 further provides the sealable vacuum port 48 through which air contained within microwells 44 may be evacuated so that air within microwells 44 does not bubble through broth in the reservoir 50 during evacuation and generate air bubbles within inoculum-broth solutions. After evacuation, sealable vacuum port 48 is subsequently sealed, temporarily or permanently, so as to generate a flow of inoculum-broth solution from reservoir 50 into the microwells 44.

To fill the microwells 44 seen in FIG. 2 with an inoculum-broth solution to be tested, pipetting system 26 of FIG. 1 dispenses a predetermined quantity of inoculum-broth solution into a reservoir 50 for each AST test array 12 carried on AST array carrier 30 of FIG. 1 at inoculum-broth dispensing station 28. When all of the reservoirs 50 have been loaded with inoculum-broth solution, transport system 16 shuttles the AST array carrier 30 to AST array vacuum filling station 34 where a clam-shell like vacuum chamber is lowered over the AST array carrier 30 and a vacuum is applied to all AST test arrays 12 carried thereon. When vacuum is applied around the test arrays 12, air is removed from all AST microwells 44 through the sealable vacuum port 48 which is in fluid communication with individual AST microwells 44 by means of microchannel 42 and 43, seen in FIG. 2, Subsequent to this evacuation process, a source of heat, for example previously heated bar having hot-feet portions or an electrical-resistant wire supported within the vacuum filling station 34 may be brought in contact with vacuum port 48 and heated by electrical current for a predetermined time to seal or close port 48 against air flow when vacuum is subsequently released. In an alternate embodiment described hereinafter, vacuum port 48 is in fluid communication with the sacrificial evaporation well 46 and the reservoir 50 and is adapted to be temporarily sealed. Once port 48 is sealed, the vacuum is released within vacuum filling station 34 and atmospheric pressure over the inoculum-broth solution in reservoir 50 causes inoculum-broth solution to flow through opening 52 into microchannels 51, 42 and 43 thereby filling the evaporation well 46 and all microwells 44 in each of the AST test arrays carried by AST array carrier 30. As the microwells 44 are filled with inoculum-broth solution, air trapped within the chamber 58 will flow into the small recessed top edge portion 60 which acts as a bubble trap within microwell 44.

Figure 2C:
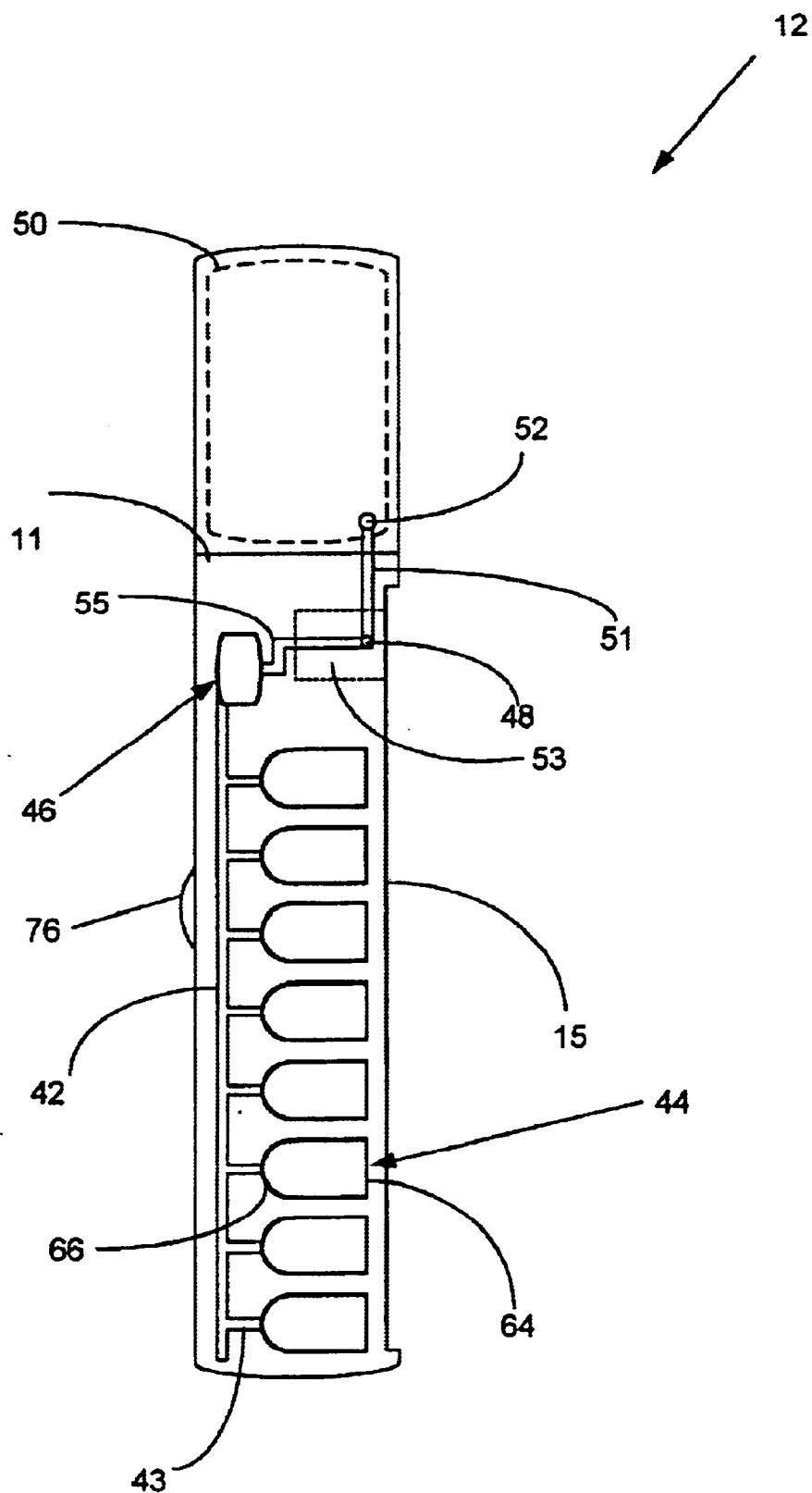
FIG. 2C is a bottom plan view of an alternate test array useful in the microbiological analyzer of FIG. 1.
Figure 3C:
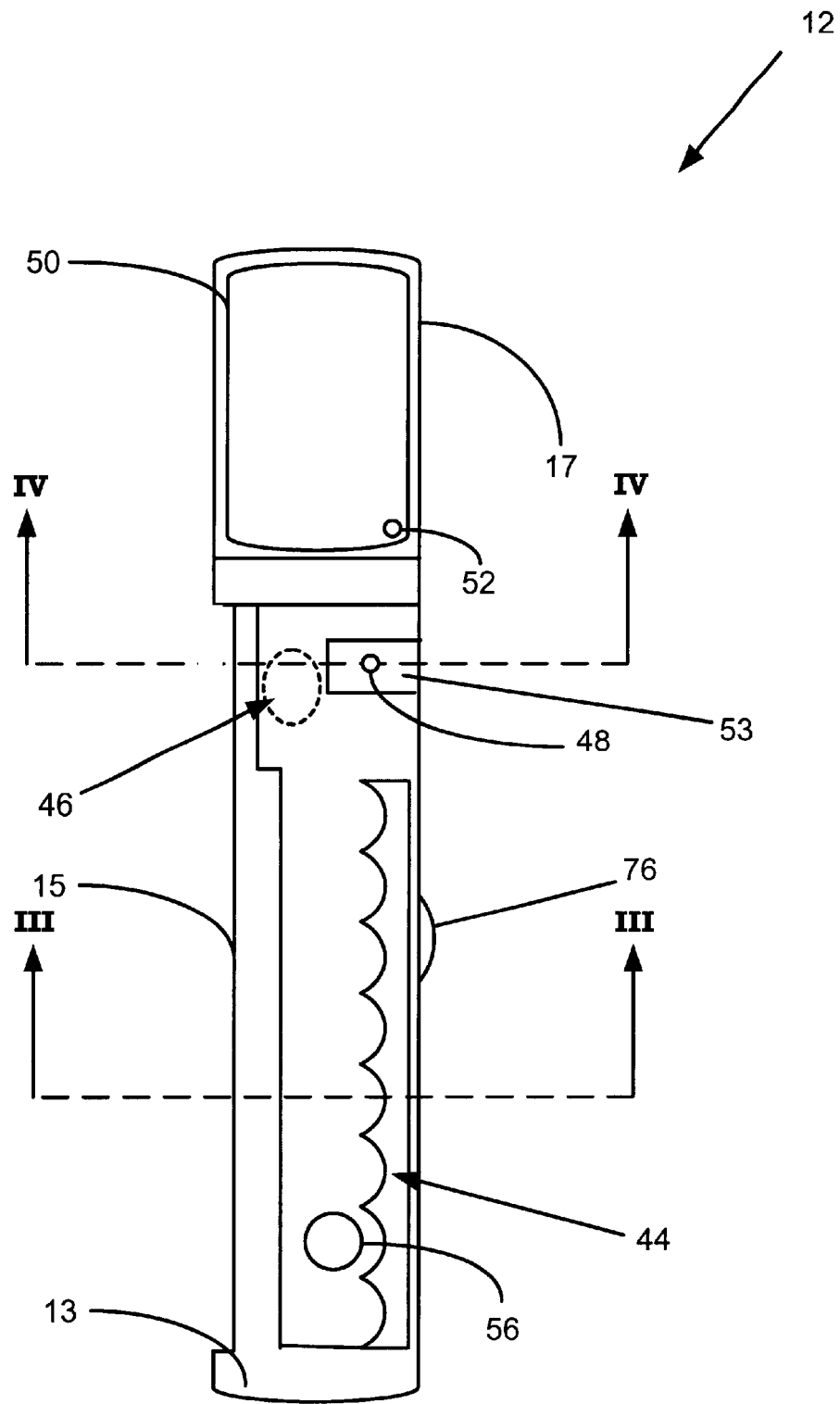
FIG. 3C is a top plan view of the test array of FIG. 2C.
Figure 3D:
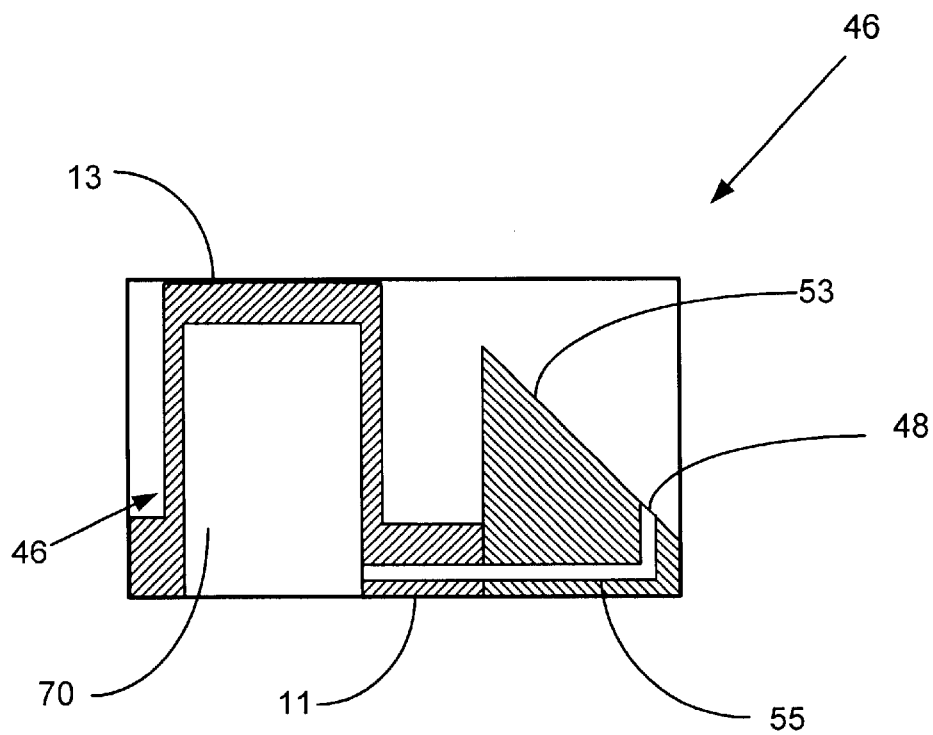
FIGS. 3D and 3E are cross-sectional views of the test array of FIG. 2C.
Figure 3E:
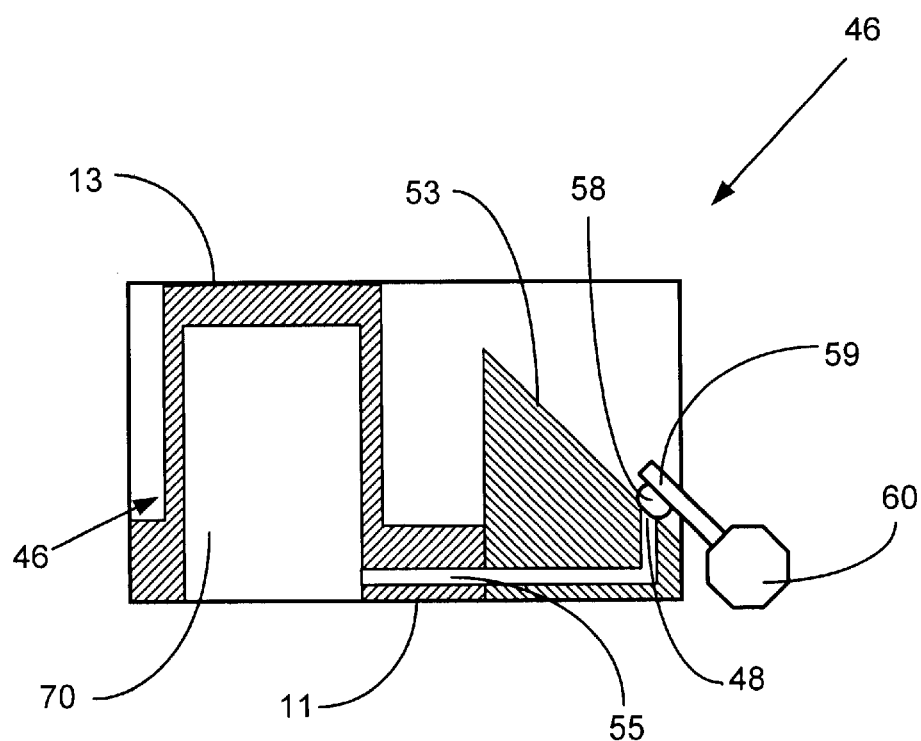

In an alternate embodiment of the present invention illustrated in FIG. 2C showing the top view of an AST array 12, taken in conjunction with FIG. 3C, showing the bottom view of an AST array 12, sacrificial evaporation well 46 may be separated from vacuum port 48 but connected thereto by a vacuum port microchannel 55. FIG. 3D is a cross-section view along lines D—D of FIG. 3C and shows such a separated arrangement of sacrificial evaporation well 46 and vacuum port 48 in an embodiment in which vacuum port 48 is seen as disposed at the upper surface of an inclined portion 53 of the upper surface 13 of AST array 12. In this embodiment, vacuum port 48 is in fluid communication with the sacrificial evaporation well 46 and the reservoir and is adapted to be temporarily sealed by a stopper pressed thereon. Thus, vacuum port 48 is not sealed by a heating action but is alternately sealed by temporarily forcing a resilient stopper 58 over the vacuum port 48 to effectively seal vacuum port against air flow during the aforedescribed vacuum filling process. This temporary sealing step is illustrated in FIG. 3E where a moveable stopper support 59 is shown as positioned by an actuator 60 so that stopper 58 effectively seals vacuum port 48 thereby to fill microwells 44 with inoculum-broth solution when vacuum is released. In a preferred embodiment, vacuum port 48 is placed as illustrated between sacrificial evaporation well 46 and reservoir 50. Alternate locations of vacuum port 48, for example, between sacrificial evaporation well 46 and microwells 44, have not given satisfactory performance. Once the vacuum is released within vacuum filling station 34 and microwells 44 are filled with inoculum-broth solution, the resilient stopper 58 may be removed from port 48.

Preferably, the AST test array 12 is constructed of a molded plastic material, but other types of material can be used. Most preferably, the material used in constructing array 12 is generally translucent, so as to allow uninterrupted transmission of light through microwells 44 during AST testing in the microbiological analyzer 10. As seen in FIG. 3, array 12 further includes a protrusion 76 formed in the sidewall 17, the protrusion 76 being generally shaped as a bulge extending from the body of the array 12 and formed in the uppermost portion of the sidewall 17. The protrusion 76 is used to facilitate loading and retention of an AST array 12 within the AST array carrier 30 and in an exemplary embodiment has dimensions of about 0.26–0.30 mm extension outward from the body of array 12, about 3–4 mm length along the edge of the array 12 and about 0.6–0.8 mm depth along the sidewall 17 of the array 12. Alternately, a high friction material such as silica or an inert powder may be coated onto the side of array 12 in place of protrusion 76 to accomplish a similar function.

AST testing may conveniently be accomplished by directing a beam of interrogating radiation from above or below each AST array 12 through the central arc portion 56 of the top surface 54 of each microwell 44 and measuring the degree of absorption or change in color or generation of a fluorescent signal using a colorimetric or fluorometric photodetector located below or above each microwell 44. For this reason, the upper center portion 56 of the top surface 54 of every microwell 44 (best seen in FIG. 3) and the lower center portion 57 of the top surface 54 of every microwell 44 are molded so as to have a surface finish smoothness equivalent to or more smooth than SPI #A-1 grade #3 diamond buff in order to minimize optical interference during AST testing.

In both of the aforedescribed embodiments of test array 12, subsequent to microwells 44 being filled with inoculum-broth solution, each one of the number of feeder microchannels 43 is sealed from the conduit microchannel 42 proximate microwell 44 (see FIG. 2 ) thereby protecting the integrity of the inoculum-broth/antimicrobial agent solution contained within the test microwells. Sealing the test microwells 44 prevents microbial organisms located in the interconnected filling microchannels 43 and conduit microchannel 42-from affecting growth within the microwells 44. This sealing process is critical to maintain the accuracy of AST testing as elsewise, microbial organisms, located in filling microchannels 43 and conduit microchannel 42, would adversely have an artificial effect of lowering the concentration of antimicrobial agents in those wells. Thus, after initial filling with a known concentration of inoculum-broth solution, an unwanted source of microbes, from the adjacent microwells 44, feeder microchannels 43 and conduit microchannel 42, will cause the signal to be measured erroneously higher due to the artificially augmented growth in the wells. The present invention, wherein the feeder microchannels 43 are sealed from the conduit microchannel 42, is thus seen as effective in protecting the integrity of the inoculum-broth solution in the test microwells 44. The term "integrity" as used herein is intended to convey the concept of being free from any material other than that originally deposited and purposefully added to the test microwells 44.

Figure 6:
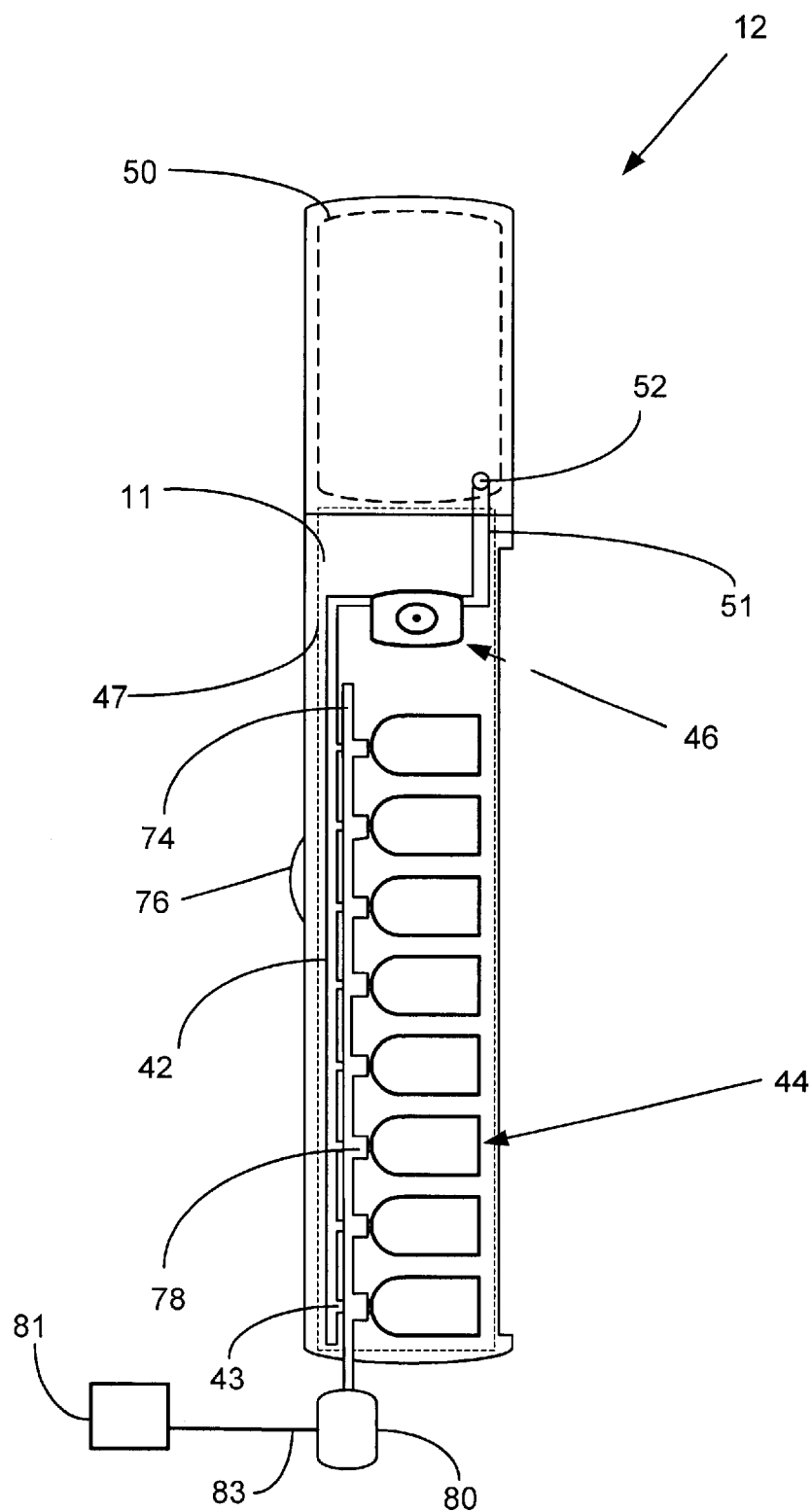
FIG. 6 is illustrative of a first microwell sealing process of the present invention.
Figure 6A:
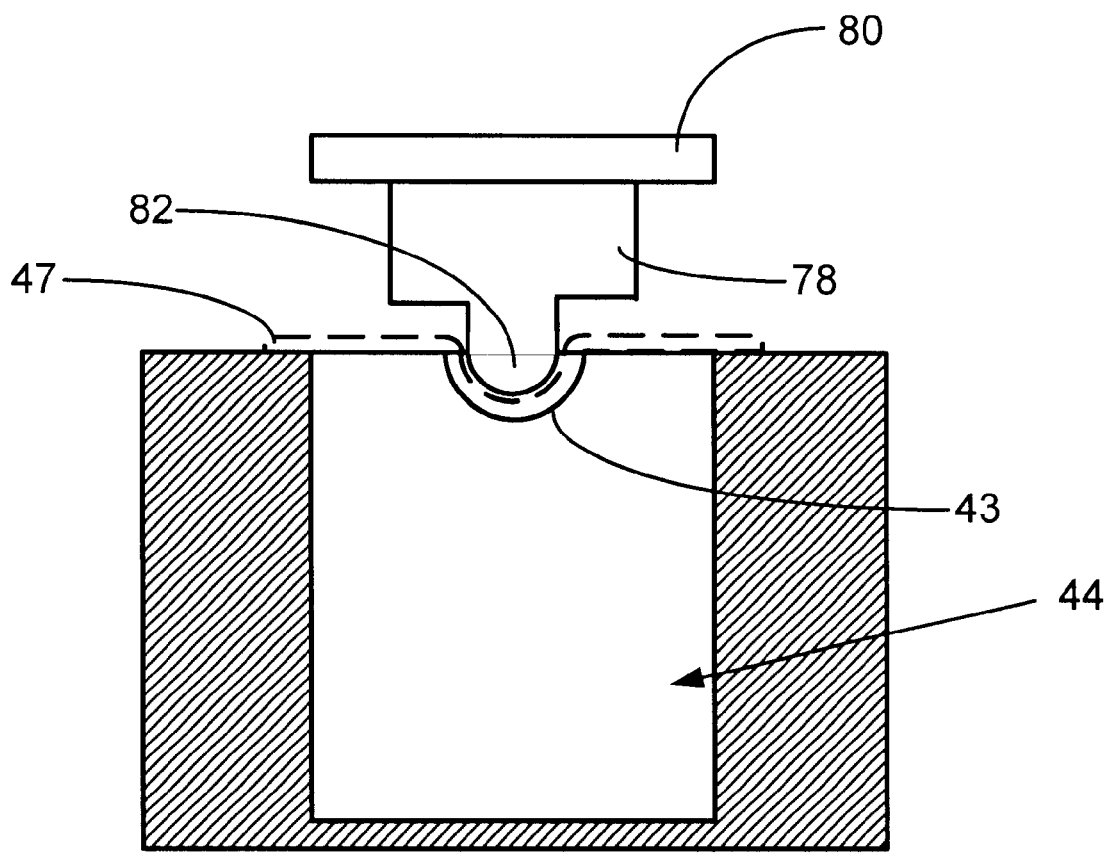
FIG. 6A is an enlarged sectional view of the microwell sealing process of FIG. 6; and, FIG. 7 is illustrative of an alternate microwell sealing process of the present invention.

FIG. 6 is illustrative of a microwell sealing process of the present invention in which a rake 74 having a number of projections 78 are simultaneously rotated by motor 80 so as to depress the layer of adhesive sealant tape 47 (in dashed lines for purposes of clarity) covering each of the filling microchannels 43 down into microchannels 43 near its entry location into microwells 44. FIG. 6A is an enlarged sectional view of the projections 78 being rotated by motor 80 and rake 74 so that projections 78 depress the layer of adhesive sealant tape 47 down into filling microchannels 43. In this illustration, projections 78 advantageously include a tip 82 shaped to mate with the microchannel 43 so that sealant tape 47 is pressed tightly into contact with microchannel 43. In a preferred embodiment, projections 78 are heated, for example by a resistance heating system 81 connected to rake 74 by wire 83, so that sealant tape 47 is partially melted when depressed into filling microchannels 43. The layer of adhesive sealant tape 47 may be heated and depressed tightly into microchannel 43 by equivalent methods such as using a downwardly inserted fork-like heated tool having tines shaped alike projections 78 to seal tape 47 into microchannel 43, and the like. Depending on the heating temperatures and times employed, next adjacent portions of into filling microchannels 43 and/or other portions of array 12 may also be partially melted when projections 78 are depressed into filling microchannels 43.

Figure 7:
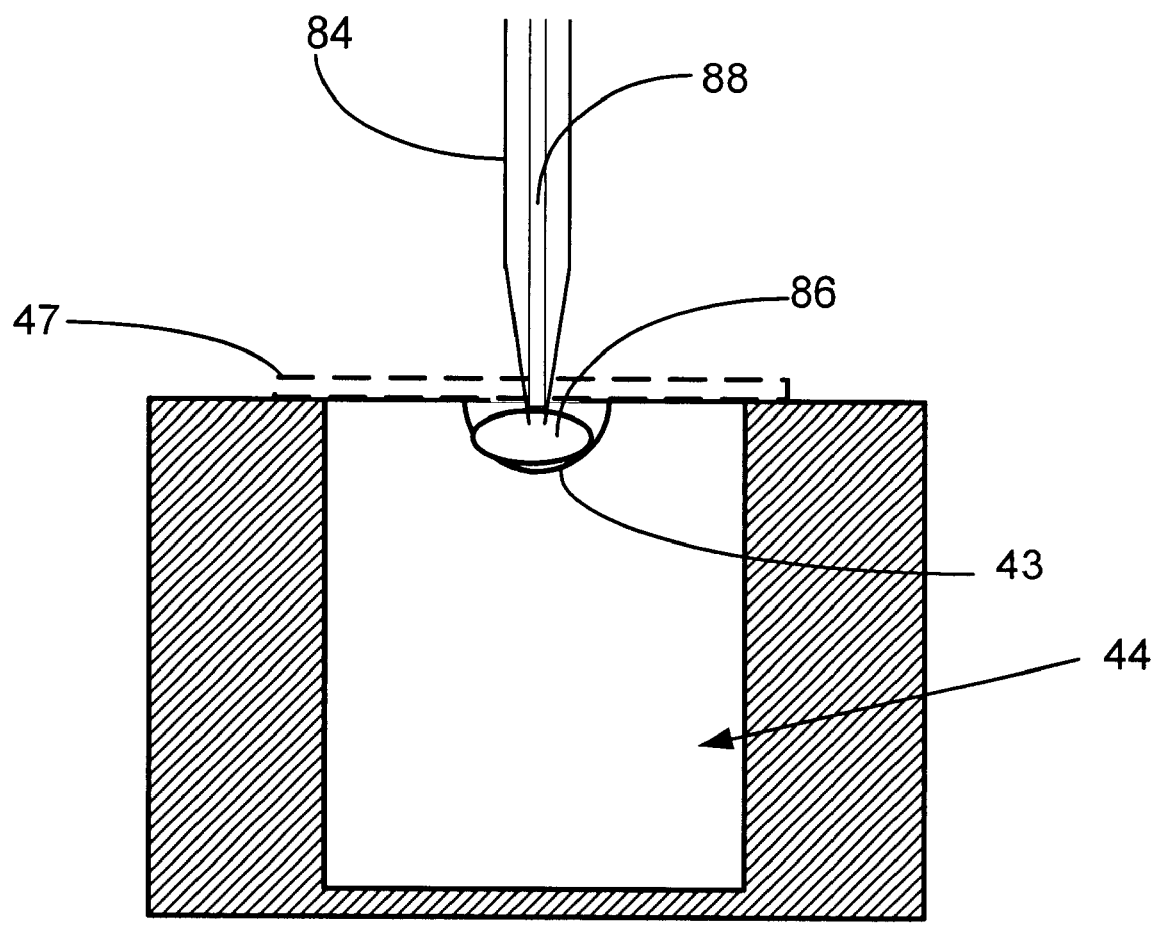

An alternate method to seal microwells 44 and protect the integrity of the inoculum-broth solution therein comprises inserting a sharp piercing needle 84 through sealant tape 47 and injecting a small droplet 86 of inert sealing material like silicone into microchannels 43 through a open channel 88 in needle 84. Such a sealing process is illustrated in FIG. 7. It is to be understood that the embodiments of the invention disclosed herein are illustrative of the principles of the invention and that other modifications may be employed which are still within the scope of the invention. For example, in a manner similar to that of FIG. 7, an inert gas like argon or the like may be pumped through channel 88 to pump all of the inoculum-broth solution remaining in filling microchannel 43 and conduit 42 back into reservoir 50 and in the array embodiment of FIG. 2C, port 48 may be closed as seen in FIG. 3E. Accordingly, the present invention is not limited to those embodiments precisely shown and described in the specification but only by the following claims.

What is claimed is:

1. A method to perform antibiotic testing of a test solution placed in a test array, the test array comprising:
- an elongate body with opposed top and bottom surfaces, said body containing a plurality of upwardly projecting test microwells adapted for test solution to be placed therein and formed in the bottom surface as a single linear row of individual microwells;
- a reservoir;
- a number of filling microchannels, each connected to a single one of the test microwells; and,
- a single conduit microchannel connecting each one of the filling microchannels to the reservoir,
- wherein the method comprises sealing the microwells by blocking the filling microchannels after test solution is placed within the microwells and prior to antibiotic testing.

2. The method of claim 1 wherein blocking the filling microchannels comprises depressing a material into the filling microchannels.

3. The method of claim 1 wherein blocking the filling microchannels comprises injecting a droplet of inert sealing material into the filling microchannels.

4. The method of claim 1 wherein blocking the filling microchannels comprises injecting a droplet of inert gas into the filling microchannels.

5. The method of claim 2 wherein the material is a layer of tape.

6. The method of claim 3 wherein the inert sealing material is silicone.

7. The method of claim 4 wherein the inert gas is argon.

8. The method of claim 5 wherein the layer of tape is heated.

9. The method of claim 1 wherein the filling microchannels are formed in the bottom surface of the elongate body.

10. The method of claim 1 wherein the single conduit microchannel is formed in the bottom surface of the elongate body.

11. The method of claim 1 wherein the reservoir is formed in the top surface of the elongate body.

* * * * *